(12) United States Patent
Szycher

(10) Patent No.: US 7,998,498 B2
(45) Date of Patent: Aug. 16, 2011

(54) ANTIMICROBIAL MATERIAL AND METHOD FOR MAKING THE SAME

(76) Inventor: Michael Szycher, Lynnfield, MA (US)

( * ) Notice: Subject to any disclaimer, the term of this patent is extended or adjusted under 35 U.S.C. 154(b) by 201 days.

(21) Appl. No.: 12/347,703

(22) Filed: Dec. 31, 2008

(65) Prior Publication Data

US 2009/0186064 A1    Jul. 23, 2009

Related U.S. Application Data

(60) Provisional application No. 61/022,609, filed on Jan. 22, 2008.

(51) Int. Cl.
*A61F 2/00* (2006.01)
(52) U.S. Cl. ........................................ 424/423
(58) Field of Classification Search .................. None
See application file for complete search history.

(56) References Cited

U.S. PATENT DOCUMENTS

| | | | |
|---|---|---|---|
| 2,943,627 A | 4/1960 | Howell | |
| 4,817,594 A | 4/1989 | Juhasz | |
| 4,895,154 A | 1/1990 | Bartelt et al. | |
| 4,982,742 A | 1/1991 | Claude | |
| 5,205,297 A | 4/1993 | Montecalvo et al. | |
| 5,320,598 A | 6/1994 | Haak et al. | |
| 5,395,398 A | 3/1995 | Rogozinski | |
| 5,445,606 A | 8/1995 | Haak et al. | |
| 6,032,077 A | 2/2000 | Pomeranz et al. | |
| 6,051,748 A | 4/2000 | Auguste et al. | |
| 6,280,434 B1 | 8/2001 | Kinoshita et al. | |
| 6,365,220 B1 | 4/2002 | Burrell et al. | |
| 6,411,853 B1 | 6/2002 | Millot et al. | |
| 6,866,859 B2 | 3/2005 | Trogolo et al. | |
| 2004/0087877 A1* | 5/2004 | Besz et al. | 600/585 |
| 2005/0064005 A1* | 3/2005 | Dinh et al. | 424/422 |
| 2005/0271698 A1* | 12/2005 | Bucay-Couto et al. | 424/423 |
| 2006/0121078 A1* | 6/2006 | Trogolo et al. | 424/422 |
| 2007/0048358 A1 | 3/2007 | Schorr et al. | |
| 2008/0014278 A1 | 1/2008 | Lu et al. | |
| 2008/0015598 A1 | 1/2008 | Prommersberger | |
| 2008/0306181 A1 | 12/2008 | Garey, Jr. et al. | |

FOREIGN PATENT DOCUMENTS

WO    WO2007000591    * 1/2007

OTHER PUBLICATIONS

Wikipedia: "Silver Sulfadiazine" (http://en.wikipedia.org/wiki/Silver_sulfadiazine) (p. 1).*
Wikipedia: "Silver Sulfadiazine" (http:llen.wikipedia.orglwikilSilver_sulfadiazine) (p. 1 ).*

* cited by examiner

*Primary Examiner* — Robert A Wax
*Assistant Examiner* — Bethany Barham
(74) *Attorney, Agent, or Firm* — William A. Loginov, Esq.; Loginov & Associates, PLLC

(57) ABSTRACT

This invention provides a modified catheter biomaterial that provides both immediate, and long-term microbiocidal effects on otherwise antibiotic-resistant strains of microorganisms. The material, which exhibits good mechanical performance characteristics for medical devices, is composed of a hydrophobic polyurethane (PU), a hydrophilic polyethylene vinyl acetate (PEVA), a soluble silver salt and a sparsely-soluble silver salt. The hydrophobic polyurethane provides the good physical properties, the PEVA the hydrophilicity necessary to allow some water ingress into the catheter, the soluble silver salt for an immediate burst effect, and the sparsely-soluble silver salt for sustained-release over many months postimplantation.

14 Claims, 3 Drawing Sheets

ANTIMICROBIAL MATERIAL AND METHOD FOR MAKING THE SAME

RELATED APPLICATION

This application claims the benefit of U.S. Provisional Application Ser. No. 61/022,609 entitled ANTIMICROBIAL MATERIAL AND METHOD FOR MAKING THE SAME, by Michael Szycher and filed Jan. 22, 2008, the teachings of which are expressly incorporated herein by reference

FIELD OF THE INVENTION

This invention relates to antimicrobial polymeric materials and their methods of manufacture and more particularly to materials suitable for medical devices that contact internal tissues.

BACKGROUND OF THE INVENTION

Catheters play critical roles in the administration of chemotherapy, antibiotics, blood, blood products and total parenteral nutrition essential for the successful treatment of many chronic afflictions. Recent advances in catheter technology have enabled their explosive growth in nephrology (hemodialysis catheters) and inpatient interventions (peripherally inserted catheters).

Unfortunately, the hydrophobic catheter surface has a very high potential of allowing microbial colonization that lead to serious and often life-threatening complications, particularly nosocomial infections. To counter this risk, catheter insertion sites are maintained scrupulously clean, which, while reducing the probability of infection cannot completely eliminate infections that significantly increase patient morbidity and mortality. Current treatments to prevent catheter-related infections rely primarily on the use of antimicrobial loaded coatings. However, the tradeoffs between thin and thick coatings severely limits the performance of these powerful coatings, since thin coatings only have limited antibacterial life, while thick coatings may last longer, but are far more susceptible to cracking, peeling and flaking-off.

Many approaches have been studied to reduce the incidence of bacterial infections associated with the use of indwelling catheters and trans-dermal implanted devices, but none have met with more than success for limited periods of time. Such infections include nosocomial infections, which are those resulting from treatment in a hospital or a healthcare service unit, but secondary to the patient's original condition. Infections are considered nosocomial if they first appear 48 hours or more after hospital admission or within 30 days after discharge. By way of background, the term "nosocomial" derives from the Greek word nosokomeion (νοσοκομείον) meaning hospital (nosos=disease, komeo=to take care of).

Nosocomial infections are even more alarming in the 21st century as antibiotic resistance spreads. Reasons why nosocomial infections are so common include:

Catheter insertions bypass the body's natural protective barriers;

Hospitals house large numbers of people who are sick and whose immune systems are often in a weakened state;

Increased use of outpatient treatment means that people who are in the hospital are sicker on average; and Routine use of anti-microbial agents in hospitals creates selection pressure for the emergence of resistant strains.

In the United States, it has been estimated that as many as one hospital patient in ten acquires a nosocomial infection, or 2 million patients per year. Estimates of the annual systemic cost resulting from such infections range from $4.5 billion to $11 billion. Nosocomial infections contributed to 88,000 deaths in the U.S. in 1995.

The risk of contracting an infection in a clinical setting is increasing every year, and the types and virulent nature of such infections continues to rise. Due, in part to the loosening of import restrictions into the U.S. under the North American Free Trade Agreement (NAFTA), as well as widespread international air travel, eco-tourism to exotic third-world forests and islands, and massive migration of third-world peoples to Europe and America, hosts of exotic diseases that were once isolated to small areas of the planet are now finding their way into U.S. and European hospitals. Eradicated for almost a century, malaria is once again returning to the U.S. and the exotic and deadly Ebola virus has broken out in a lab in Maryland. Shigella (which causes dysentery) was practically unheard of in America before 1990, but it is now being spread from contaminated fruits and vegetables imported into the U.S. under the auspice of the NAFTA treaty, and is now routinely seen at clinics in California.

Of potentially greater concern is that many common strains of microorganisms have become increasingly resistant to a wide range of antibiotics (due to incomplete kills and simple natural selection). Many strains must be treated with one or two "last-resort" antibiotics and new compounds must be continually developed to combat these evolving strains. By way of example, some common (and dangerous) germs such as *Staph aureus* (found especially in hospitals) are now known to be resistant to all but one antibiotic—vancomycin—and soon are expected to be vancomycin-resistant as well. According to the Centers for Disease control, in 1992, 13,300 hospital patients died [in the U.S.] of bacterial infections that resisted the antibiotics administered to fight them.

Generally, antibacterial agents inhibit or kill bacterial cells by attacking one of the bacterium's structures or processes. Common targets are the bacterium's outer shell (called the "cell wall") and the bacterium's intracellular processes that normally help the bacterium grow and reproduce. However, since a particular antibiotic typically attacks one or a limited number of cellular targets, any bacteria with a resistance to that antibiotic's killing mechanism could potentially survive and repopulate the bacterial colony. Over time, these bacteria could make resistance or immunity to this antibiotic widespread.

Silver, platinum and gold, which are elements of the noble metals group, have long been known to have medicinal properties. For example, platinum is the primary active ingredient in cisplatin, a prominent cancer drug. Similarly, gold is the active agent in some treatments for rheumatoid arthritis. More particularly, unlike its heavy metal counterparts, silver (atomic symbol Ag) with atomic element number 47 and an atomic weight of 108, is surprisingly non-toxic to humans and animals, and has a long history of successful medical and public health use dating back 6000 years. Also, unlike antibiotics, silver has been shown to simultaneously attack several targets in the bacterial cell and therefore it is less likely that bacteria would become resistant to all of these killing mechanisms and create a new silver-resistant strain of bacteria. This may be the reason that bacterial resistance to silver has not been widely observed despite its centuries-long use. This can be particularly important in hospitals, nursing homes and other healthcare institutions where patients are at risk of developing infections.

By way of further background, from 1900 to the beginning of the modern antibiotic era—circa 1940 with the introduction of sulfa drugs—silver and its ionic and colloidal compounds (silver nitrate, for example) was one of the mainstays of medical practice in Europe and America. Various forms of silver were used to treat literally hundreds of ailments: lung infections such as pneumonia, tuberculosis and pleurisy; sexual diseases such as gonorrhea and syphilis; skin conditions such as cuts, wounds, leg ulcers, pustular eczema, impetigo and boils; acute meningitis and epidemic cerebro-spinal meningitis; infectious diseases such as Mediterranean fever, erysipelas, cystitis, typhus, typhoid fever, and tonsillitis; eye disorders such as dacryocystitis, corneal ulcers, conjunctivitis and blepharitis; and various forms of septicemia, including puerperal fever, peritonitis and post-abortion septicemia. An even larger list of the published medical uses for silver in Europe and America exists between 1900-1940.

Sparsely-soluble silver salts are composed of large microcrystals, usually several microns in diameter or greater. These microcrystals dissolve extremely slowly, thereby limiting the rate and amount of silver ion released over time. By converting the salt's microscaled structure into an atomically nanoscaled structure, it tremendously increases the surface area, thus enhancing silver ion release and efficacy characteristics and thereby making it a more potent antimicrobial agent.

The provision of silver in a releasable form for use in an anti-microbial application is discussed, for example, in U.S. Pat. No. 6,821,936, entitled TEXTILES HAVING A WASH-DURABLE SILVER-ION BASED ANTIMICROBIAL TOPICAL TREATMENT, by David E. Green, et al., the teachings of which are expressly incorporated herein by reference. This patent provided a coating of an anti-microbial silver-salt-based treatment to fabric threads to resist the buildup of bacteria on a fabric. While this approach may be effective for fabrics, it and other silver-based solutions have certain drawbacks when applied to catheters and other invasive devices. First, when a coating is applied, for example to the lumen or exterior of a catheter, it changes the diameter of that catheter. The insertion of a guidewire, syringe tip or other close-conforming structure will tend to abrade the anti-microbial coating, again exposing the underlying, unprotected surface of the catheter/device. In addition these coatings are either designed to last long term, with very few silver atoms/ions released to the environment by the use of sparingly soluble silver compounds, or release all of their exposed soluble silver salt very quickly. This is because they are not adapted to exist within an implanted environment, where there is a constant source of new bacterial infiltration via the open wound channel. Also, because the coatings are relatively thin, they exhaust the available supply of silver salt (which is exposed at the coating surface) in a relatively short time.

It is, thus, desirable to provide a structural polymer, for which the implanted and exposed portion of the device is constructed, that contains the anti-microbial silver compound as an integrated part of its composition. However, the creation of a structural material that contains an embedded supply of silver is not trivial. The embedded silver may either release too slowly, or not at all if the material is not sufficiently hydrophilic. A hydrophilic material allows the needed ion exchange via interaction of the material with adjacent bodily fluids/water. Absent infiltration of water, deeper embedded silver will never have the chance to release, and only the material's surface silver is released. However, if the material is too hydrophilic, it may not exhibit the necessary structural strength to act as an invasive or implanted device or the material may undesirably swell as it absorbs bodily fluids causing the device to fall outside needed size tolerances. It is also not trivial to provide a material with the proper degree of hydrophilicity, while maintaining desired structural characteristics, and releasing silver at a desired rate. This goal typically calls for a polymer blend, and most polymers do not blend well—if at all. Adding a silver-containing compound only complicates the blending. Moreover, while some silver compounds may be blendable, industry often desires that the resulting device be clear or translucent and typically uncolored. Many silver containing compounds exhibit dark and/or undesired colors upon heating or exposure to light.

The challenge of developing a structural polymer is further complicated by a desired to quickly treat any existing infections or the large initial introduction of bacteria when inserting a device with a large, short-time-released dose of silver, and then providing a lower, continuing dose to ward off any re-infection. Accordingly it is desirable to provide a silver-compound-containing material that satisfies all of these often-competing goals.

SUMMARY OF THE INVENTION

This invention overcomes the disadvantages of the prior art by modifying one of the most commonly used catheter biomaterials in such a manner as to drastically reduce infections during the long periods that such catheters must remain within the body. This modification appears to have not only the potential to be medically effective, but also to allow the fabrication of improved indwelling catheters with minimal increase in cost. In particular, the modification includes the use of the noble metal, silver in, for example, nanoargentic form, which fulfills a large unmet need for effective, locally administered antimicrobial products that are not susceptible to bacterial resistance.

In an illustrative embodiment, the modified catheter biomaterial is composed of a hydrophobic polyurethane (PU), a hydrophilic polyethylene vinyl acetate (PEVA), a soluble silver salt and a sparsely-soluble silver salt. The hydrophobic polyurethane provides the good physical properties, the PEVA the hydrophilicity necessary to allow some water ingress into the catheter, the soluble silver salt for an immediate antimicrobial burst effect, and the sparsely-soluble silver salt for sustained-release antimicrobial effect over many months postimplantation. This compound should prove superior to anything currently available since it offers immediate plus long-term protection at a low manufacturing cost.

In illustrative embodiments, a medical device formed from the antimicrobial material can comprise a variety of indwelling devices including various types of indwelling catheters in which the attraction and/or colonization of microbes/bacteria (or formation of biofilms) on surfaces thereof is desirable prevented. In further embodiments, layers of material having various compositions and/or concentrations of polymers and/or silver ionic salts can be coextruded or otherwise formed into a single unitary/integral structure. This structure can define concentric layers of a catheter shaft wall.

BRIEF DESCRIPTION OF THE DRAWINGS

The invention description below refers to the accompanying drawings, of which.

DETAILED DESCRIPTION

Figure 1:
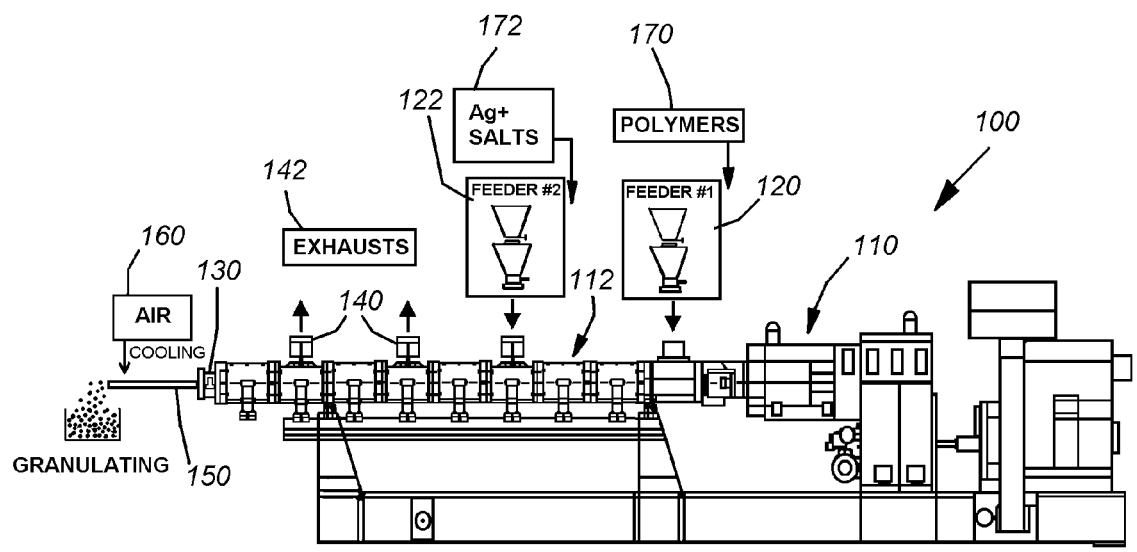
FIG. 1 is an exemplary twin-screw compounding extruder employed in performing a one-stage melt process by which the polymer and silver-containing compounds are mixed and formed into a predetermined structural shape in accordance with an illustrative embodiment of this invention.

FIG. 1 illustrates a complete, one-stage melt process for the exemplary antimicrobial polymeric material according to an illustrative embodiment of this invention. The process employs the depicted twin-screw compounding extruder 100. The basic operative components of the extruder 100 are well-known in the art, and not described in further detail. In general, the mechanical system of the extruder 100 is driven by a motorized drive 110. This drive rotates twin feed and mixing screws (not shown) housed within a series of interconnected, heated mixture housings 112. The housings 112 are connected to a pair of feeders (feeder #1 (120) and feeder #2 (122)), each of which allow a predetermined component of the mixture to be added to the mix. The fed components are completely mixed as they are driven downstream toward the extrusion die head 130. A plurality of exhaust ports 140, allow removal of any residual mixture in the extruded material. The extruded structure 150, composed of the mixed, melted material is output from the die head 130 with an appropriate cross-sectional shape (defined by the cuts of the die). Air 160 can be blown over the output extrusion to cool it into a solidified state palletized/granulated state for later use in an extruder or other melt-based formation process (e.g. molding). Conversely, the output material can be formed into a finished profile extrusion. This extrusion can then be cut into desired lengths as appropriate.

In this illustrative embodiment, a polymer mixture 170 of polyurethane and PEVA is added gravimetrically in feeder #1 (120), and a mixture 172 of silver salts, radiopacifiers and colors (among other additives) is added gravimetrically to the melt in feeder #2 (122). The components for forming the illustrative structural polymeric antimicrobial material, and their relative contributions to the material's properties will now be described in further detail.

The structural material for use in forming catheters and other devices that come into contact with exposed wounds and internal tissues can be constructed from a combination of four basic components. By way of example, these components can be mixed together in a solution of dimethyl acetamide (or another non-polar acceptable solvent), which causes the compounds to dissolve and intermix. Notable, it has been determined that a combination of relatively hydrophobic, but structurally durable and ductile poly(carbonate) urethane polymer, also simply termed polyurethane (PU), can be mixed with relatively hydrophilic polyethylene vinyl acetate (PEVA) polymer to form a compatible polymer blend with the requisite degree of hydrophilicity. The PEVA is approximately 0.5-1.0% to 20.0% by weight of the resulting mixture. This combination, when mixed displays a relatively clear appearance, denoting a complete blending of polymer compounds.

The combination of PU and PEVA is then provided with approximately 0.1%-1% to 5.0%-10% by weight by weight of a relatively soluble silver compound that releases ionic silver to the wound site over a short period of time based upon the ability for bodily water to ingress into the PEVA. An acceptable quick-release silver compound is silver trifluoro acetate. Alternatively, silver nitrate, or another soluble silver salt can be substituted at a suitable concentration within the material, such as silver lactate, or silver benzoate.

The compound also contains approximately 0.1%-1% to 5.0%-15% by weight of a sparingly soluble, or nearly insoluble silver salt that releases from the material at a substantially slower, but relatively constant rate. One material that may be employed for this function is silver stearate. Other sparingly soluble silver-salt materials can also be employed, such as silver iodate, silver zeolite, silver zirconium phosphate or silver soluble glass.

In continuous melt production, these materials can be mixed within the gravimetric feeders of a twin-screw extrusion device with an extrusion die having (1) the ability to produce pellets, (2) any desired catheter profile, or (3) the profile of another device. In an illustrative embodiment the material from which medical devices are constructed consists of CarboThane PC-3485A-B20, (the structural thermoplastic polyurethane component of the overall material mixture), a product commercially available from Lubrizol Advanced Materials, Inc. of Wilmington, Mass., and Elvax 470 (the hydrophilic polyethylene vinyl acetate (PEVA) component of the material mixture) a product commercially available from the DuPont Company of Wilmington Del. The illustrative twin screw compounding extruder intimately mixes the two polymers together, and contemporaneously incorporates the appropriate silver salts all in one operation of the exemplary extruder.

To construct more-complex devices other than extruded tubing, appropriate mold cavities, which receive the mixed compound components can also be employed during the compounding operation.

In an experimental procedure, using a commercially-available, medical grade polyurethane (PU) solution (available, for example from ChronoFlex AR, CardioTech International, Inc. of Woburn, Mass.), silver salt(s) is/are manually incorporated into the solution. The silver-loaded ChronoFlex solution is spread onto glass, and dried in a circulating oven at 80 C for 1.5 hours. The loaded PU film was allowed to equilibrate at RT for at least two days, and subsequently demolded. The film was manually cut into circles by means of a cork borer, and placed into serially-labeled Petri dishes. The microbiology technician was blinded regarding which silver salts were incorporated into the film. Two types of silver salts were tested as described generally above: (1) soluble salts for quick release, and (2) an insoluble salt for longevity. The two candidate soluble salts were silver trifluoroacetate, and silver nitrate, and the relatively insoluble salt tested was silver stearate.

A standard in vitro agar zone of clearing test (better known as zone of inhibition test), after 24 hours of exposure, was conducted. If the test samples show a "zone of inhibition" ("ZOI") the specimen thus display the capacity to kill the microorganisms tested. The ZOI is measured in mm; the greater the ZOI distance, the more powerful is the microbiocidal effect. Note that, prior to application, the test films were sterilized using short-wave UV at a distance of 2 inches for 10 seconds.

Both of the subject, soluble silver salts exhibited a large zone of inhibition clearing against both *s. aureus* and *p. aeruginosa*. The insoluble salt showed no microbiocidal activity at 24 hours, which was expected, as its active period should be significantly longer in time, and less aggressive toward the test strains. The following table records the observed ZOI measurement for the control PU material (no active compound) and for each active compound within the PU material. Using a 10 mm sample disc, the microbial growth inhibition was measured from the edge of each sample disc, producing antimicrobial results in accordance with the following Table:

| Sample identification | S. aureus ZOI (mm) | P. aeruginosa ZOI (mm) | MRSA ZOI (mm) |
|---|---|---|---|
| Control polyurethane (PU) CarboThane PC-3485A-B20 | 0 | 0 | 0 |
| PU + Silver trifluoro acetate plus silver stearate | 6 | 7 | 6 |
| PU + EVA + silver trifluoro acetate | 12 | 10 | 11 |
| PU + EVA + silver stearate | 6 | 4 | 6 |
| PU + EVA + silver nitrate | 13 | 9 | 11 |
| PU + EVA + silver iodate | 4 | 3 | 4 |
| PU + EVA + silver lactate | 2 | 3 | 2 |
| PU + EVA + silver benzoate | 2 | 8 | 2 |
| PU + EVA + silver trifluoro acetate + silver iodate | 14 | 12 | 13 |
| PU + silver acetate | 2 | 3 | 2 |
| PU + silver stearate | 0 | 0 | 0 |
| PU + silver trifluoro acetate | 8 | 2 | 7 |
| PU + silver nitrate | 10 | 6 | 10 |
| PU + silver iodate | 2 | 1 | 2 |
| PU + silver lactate | 0 | 2 | 0 |
| PU + silver benzoate | 0 | 5 | 0 |

It should be noted that of all ionic silver compounds tested, only silver iodate discolored only slightly, an significant consideration in the manufacture of light-colored medical devices. Most of the other silver salts were photosensitive. As reported in the Table above, silver trifluoro acetate (a very soluble salt) combined with silver iodate (a less soluble salt) provides a highly effective material, that is also substantially free of undesired discoloration.

In the above-described initial tests, the illustrative compounds exhibits rapid antimicrobial activity, killing many organisms within 30 minutes of application, which is faster than many other commercially-available forms of antimicrobial silver. These organisms include gram positive (*staphylococcus aureus*) and gram negative bacteria (*pseudomonas aeruginosa*), and also including some antibiotic resistant strains. It is recognized that the inclusion of PEVA in the proportions defined generally above would serve to enhance the delivery of silver compounds beyond the film surface, allowing the killing action of the compound to be extended for longer periods of time and in greater delivery concentrations for both the soluble and insoluble salts. Qualitative observation of batches of PU-PEVA materials as described in the Table above, have shown good strength and ductility, without flaking, brittleness or cracking, making it suitable for the construction of catheters and other invasive and/or implantable medical devices.

Figure 2:
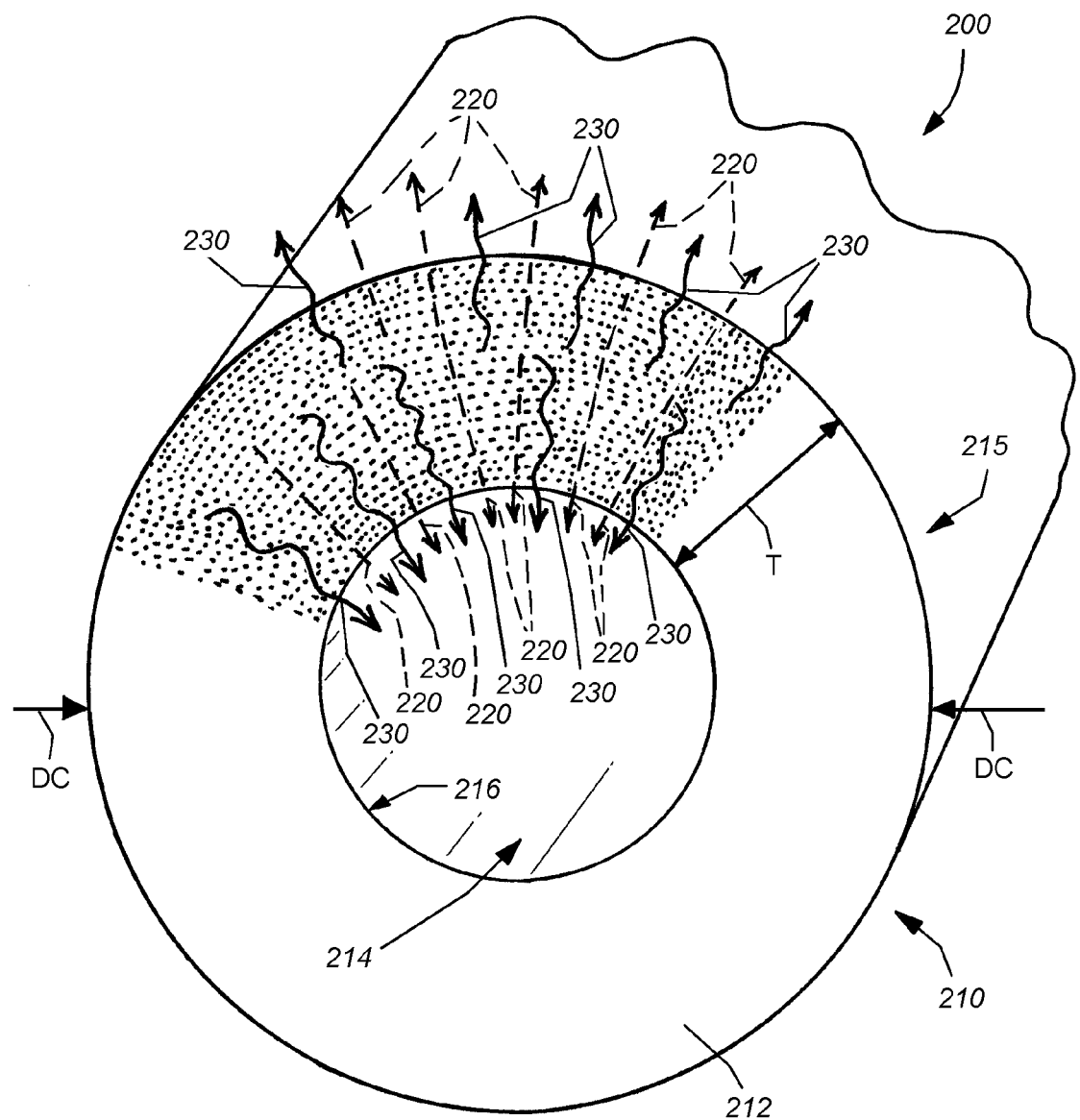
FIG. 2 is a perspective cross sectional view of an exemplary catheter, of any of a number of types, constructed from the material of an antimicrobial polymer according to an illustrative embodiment of this invention showing the migration of antimicrobial ionic material from all catheter surfaces.

The antimicrobial action of a finished device constructed from the illustrative polymer material is shown in FIG. 2. As illustrated, the exemplary device 200 comprises a flexible, cylindrical catheter shaft 210 having a wall 212 and a central lumen 214. The wall 121 is defined by an outer shaft surface 215 an inner luminal surface 216. The opposing surfaces 215, 216 of the wall 212 can be separated by any appropriate radial wall thickness T, and the overall diameter DC of the shaft with respect to the outer surface can be any diameter adapted for insertion and/or implantation into a patient's body. Of course, the catheter need not define a cylindrical cross section, but can be another cross section such as a polygon, oval, irregular enclosed shape, and the like.

As shown in FIG. 2, the soluble salts are drawn rapidly from the material (dashed arrows 220) around the entire inner and outer perimeter of the device 200 (depicted only partially for clarity). The salts thereby migrate onto the outer surface 215 and its environs within the implantation site, and also onto the inner luminal surface 216, and to an extent, into the fluid medication carried by the lumen 214. As noted, this initial rapid migration provides a burst of antimicrobial activity beneficial in the initial implantation of the device (where an elevated level of microbes may have entered the site). As the ionic silver salts used herein are non-toxic in the quantities administered (and in fact may be beneficial), the presence of these salts in the treatment stream of fluid should provide no negative effects to the patient. The use of Elvax 470 (or another hydrophilic material) in concentrations of between 0.5%-2% and 20% of total weight (and approximately 5% in this example) creates the desired conduit for water to transfer the soluble salt relatively rapidly from deep within the thickness. Without such a conduit, the silver ionic compounds would be capable of migration only from the surface in appreciable quantities from a mainly hydrophobic PU-based material. The same PEVA-based water conduit also helps to more-gradually dissolve the less-soluble salts as exemplified by wavy arrows 230 that extend onto and out of both the outer surface 215 and inner luminal surface 216. This dissolution (wavy arrows 230) occurs over a substantially longer time period as described above, allowing for the long-acting antimicrobial effect. As also shown, the draw of such salts, while occurring more slowly, derives from deep within the thickness. Thus, the material efficiently exhausts a significantly larger quantity of the overall contained ionic antimicrobial filling, than a less-hydrophilic material would allow.

While the antimicrobial polymer material of the illustrative embodiments can be employed to construct all or part of a variety of implanted and implantable devices, a highly beneficial aspect is provided to various indwelling catheters where the prevention of bacterial attachment, microbial colonization and growth of biofilms on any surfaces thereof is critical. Hence, the catheter device 200 can be representative of the general indwelling shaft portion of a variety of types of catheters including, but not limited to a (a) Chronic Dialysis Catheter; (b) Central Venous Catheter; (c) Peripherally Inserted Central Catheter; (d) Urinary Catheter; and (e) Gastrostomy Catheter. In any illustrative catheter contemplated herein, additional lumens, steering, guiding and other useful structures can be provided to the depicted shaft without departing from the teachings of this invention.

Figure 3:
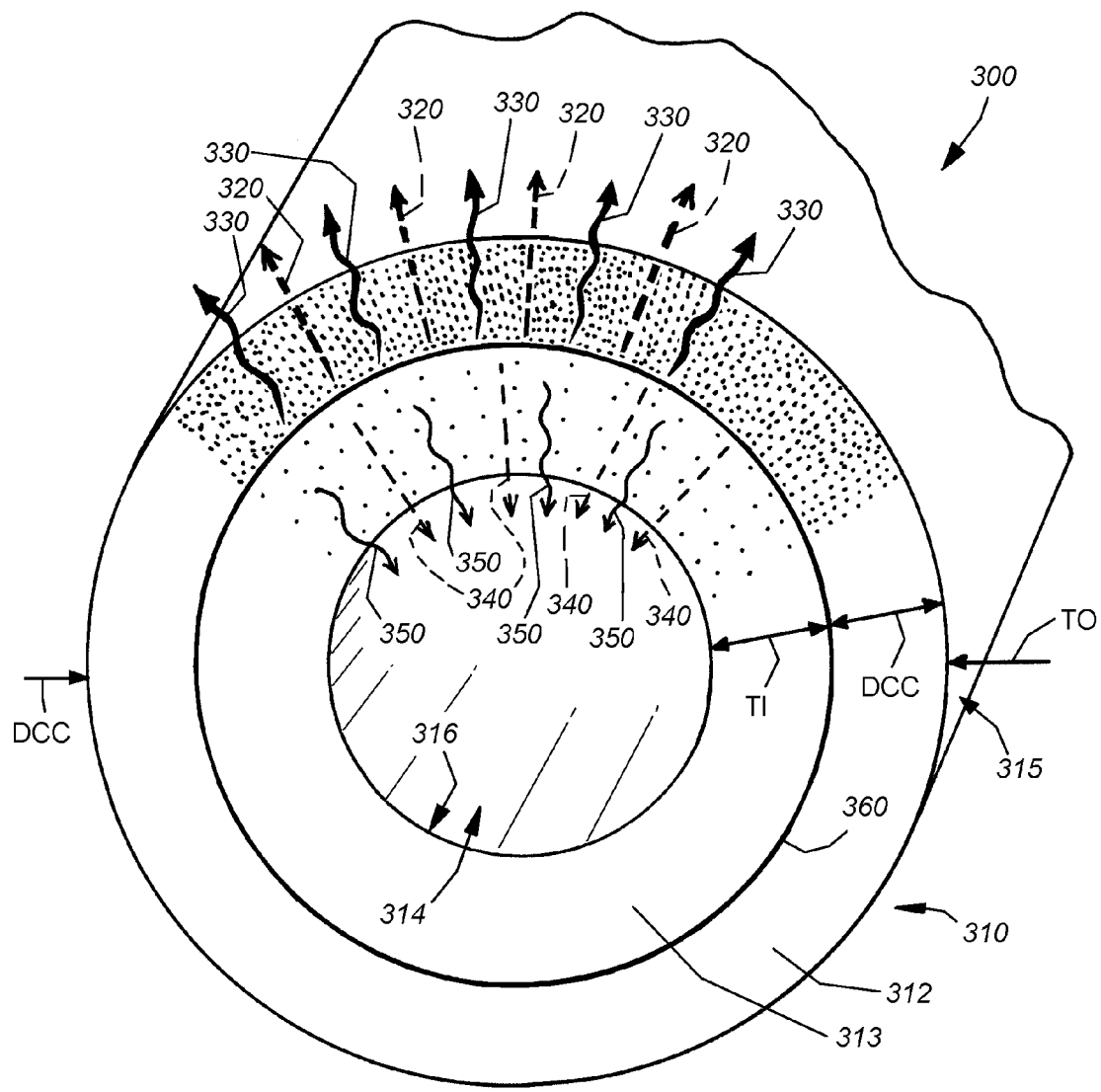
FIG. 3 is a perspective cross sectional view of an exemplary catheter, of any of a number of types, constructed from at least two layers of the material of an antimicrobial polymer, each layer having differing diffusion properties, according to an illustrative embodiment of this invention showing the migration of antimicrobial ionic material from all catheter surfaces.

Of course the illustrative PEVA used herein can be substituted with another material (or plurality of materials) that is miscible with the base (normally hydrophobic) material and provides a hydrophilic conduit-producing structural material. Likewise, while a single layer of uniform material is used in various embodiments to construct a device, conventional techniques can be used to co-extrude (or otherwise form) a device wall having a plurality of material layers, each having different material compositions. For example, material exhibiting a slower ionic compound release can be provided near the exterior surface, while materials exhibiting a faster ionic release can be located deeper within the wall—or vice versa. Likewise, higher concentrations of ionic compound can be placed in a deeper layer for longer release time. Accordingly, FIG. 3 depicts such a coextruded embodiment of a catheter device 300. In this embodiment, the catheter shaft 310, which can be any acceptable type of indwelling device, defines a pair of concentric, inner and outer wall structures 312 and 313, respectively. Each wall structure 312 and 313 has an associated wall thickness TO and TI that collectively (unitarily or integrally) define the overall wall thickness DCC between the outer surface 315 and the inner luminal surface 316 (which defines lumen 314). In this exemplary embodiment, the material of the outer wall structure 312 is provided with generally higher concentrations of one or both ionic silver salts, as depicted by the thickened dashed arrows 320 (rapidly soluble salts) and wavy arrows 330 (slower dissolving salts). This provides higher concentrations of released salts on and from the outer surface, which is in contact with penetrated tissue. The material of the inner wall structure 313 can contain lower concentrations of one or both salts to provide less salt on or from the inner luminal surface 316, which is generally in communication with sterile fluids. Likewise the composition of the polymers in each layer can also vary. In general, a lower concentration nearer through the inner surface with produce less migration of both more soluble and less soluble salts as depicted by the thin dashed arrows 340 and thin wavy arrows 350, respectively. Some compound may cross the margin 360 between wall structures 312, 313. In alternate embodiments, this factor can be controlled co-extruding a thin a third impermeable layer (for example, pure PU) at the margin 360, or otherwise providing a substantially impermeable barrier between different layers.

It should be clear that a variety of implantable devices, as well as catheters, can be provided with multiple layers of, or differing portions (for example catheter tips) having differing compositions of salts and/or polymers. In various embodiments, some layers or portions can omit either the more-soluble or less soluble salt, where the omitted compound's effects are not desired. Also, while construction of layers or portions with differing antimicrobial characteristics using co-extrusion is described, any acceptable manufacturing and/or assembly technique can be employed in alternate embodiments. For example different portions/layers can be adhered, fastened, co-molded, welded together, interlocked, force-fitted, or otherwise joined in alternate embodiments. Note, as used herein the term "composition" in connection with a portion or layer of the device shall refer to a predetermined mixture at least some of PU, PEVA, soluble ionic silver salt and sparsely ionic silver salt. Some or all of these components (and other additional components as desired) can be provided to the material of each portion or layer.

The foregoing has been a detailed description of illustrative embodiments of the invention. Various modifications and additions can be made without departing from the spirit and scope if this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the compound of this invention can be formed by a variety of mixing techniques using a variety of solvents. In addition, a combination of two or more soluble silver salts and/or two or more sparsely soluble silver salts can be combined in a material so the material can benefit from differing performance characteristics of each of the multiplicity of salts. Also, a finished device constructed from the illustrative material can be constructed by any acceptable mechanism, including, but not limited to, extrusion, injection molding, blow molding and the like. It should also be recognized by those of ordinary skill that the compound described herein can be applied to any acceptable device or shape in which anti-microbial properties are desired, including, but not limited to implantable device, artificial organs, surgical instruments and consumer products. Accordingly, this description is meant to be taken only by way of example, and not to otherwise limit the scope of this invention.

What is claimed is:

1. A method for producing an antimicrobial material comprising the steps of:
    (a) providing polyurethane (PU) to a solvent solution;
    (b) providing polyethylene vinyl acetate (PEVA) to the solvent solution in a predetermined amount;
    (c) providing a soluble ionic silver compound to the solvent solution in a predetermined amount; and
    (d) forming a unitary predetermined shape using a one-stage melt process that combines the solution of steps (a), (b) and (c) all in one operation to output the unitary predetermined shape, and thereafter removing the solvent.

2. The method as set forth in claim 1 further comprising, before step (d), (c)(i) providing a sparsely soluble ionic silver compound to the solvent solution in a predetermined amount.

3. The method as set forth in claim 2 wherein step (d) includes mixing each of the PU, PEVA, soluble ionic silver compound and sparsely soluble ionic silver compound in and directing the mixture through a die of a twin-screw extruder.

4. The method as set forth in claim 2 wherein the sparsely soluble ionic silver compound comprises silver iodate.

5. The method as set forth in claim 4 wherein the PEVA is between 2% and 20% by weight of the antimicrobial material.

6. The method as set forth in claim 5 wherein the soluble ionic silver compound is between 1 and 10% by weight of the antimicrobial material.

7. The method as set forth in claim 5 wherein the sparsely soluble ionic silver compound is between 1 and 15% by weight of the antimicrobial material.

8. The method as set forth in claim 2 wherein the soluble ionic silver compound is silver trifluoro acetate.

9. The method as set forth in claim 1 wherein the antimicrobial material comprises a wall of a medical device constructed and arranged to contact internal tissue and fluids of a patient.

10. The method as set forth in claim 9 wherein the wall defines an indwelling catheter.

11. The method as set forth in claim 10 wherein the indwelling catheter comprises a Chronic Dialysis Catheter.

12. The method as set forth in claim 10 wherein the indwelling catheter comprises a Peripherally Inserted Central Catheter.

13. The method as set forth in claim 10 wherein the indwelling catheter comprises a Urinary Catheter.

14. The method as set forth in claim 10 wherein the indwelling catheter comprises a Gastrostomy Catheter.

\* \* \* \* \*